United States Patent [19]

Yano et al.

[11] Patent Number: 5,559,102
[45] Date of Patent: Sep. 24, 1996

[54] ADENOSINE AND GUANOSINE-3'-5'-CYCLIC METHYLPHOSPHONATE DERIVATIVES

[75] Inventors: Junichi Yano, Nara; Tadaaki Ohgi, Otsu; Koichi Ishiyama, Oyamazaki; Kazuko Hirabayashi, Kyoto, all of Japan

[73] Assignee: Nippon Shinyaku Company, Limited, Japan

[21] Appl. No.: 181,231

[22] Filed: Jan. 13, 1994

Related U.S. Application Data

[63] Continuation-in-part of Ser. No. 996,504, Dec. 23, 1992, abandoned, which is a continuation of Ser. No. 394,524, Aug. 16, 1989, abandoned.

[30] Foreign Application Priority Data

Aug. 16, 1988 [JP] Japan .................. 63-203452

[51] Int. Cl.⁶ .................. A61K 31/70; C07H 19/167; C07H 19/173
[52] U.S. Cl. .................. 514/46; 514/47; 536/26.12; 536/26.13
[58] Field of Search .................. 536/26.12, 26.13; 514/47, 48

[56] References Cited

U.S. PATENT DOCUMENTS

| | | | |
|---|---|---|---|
| 3,560,478 | 2/1971 | Myers | 536/26.14 |
| 4,058,659 | 11/1977 | Robins et al. | 536/26.14 |
| 4,401,808 | 8/1983 | Yamaji et al. | 536/26.14 |
| 4,567,254 | 1/1986 | Kataoka et al. | 536/26.14 |
| 4,873,227 | 10/1989 | Ikada et al. | 514/47 |

FOREIGN PATENT DOCUMENTS

| | | |
|---|---|---|
| 0044527 | 1/1982 | European Pat. Off. . |
| 0061001 | 9/1982 | European Pat. Off. . |
| 0354246 | 2/1990 | European Pat. Off. . |
| 1135914 | 1/1960 | Germany . |
| 50-46689 | 4/1975 | Japan . |
| 62-42997 | 2/1987 | Japan . |
| 135399 | 6/1988 | Japan . |
| 8401778 | 5/1984 | WIPO . |

OTHER PUBLICATIONS

Meyer, Jr. et al. J. Med. Chem. vol, 16, pp. 1319–1323 (1973).

Meyer, Jr. et al. Life Sciences 14:1019–1040, 1974.

*Primary Examiner*—Gary L. Kunz
*Attorney, Agent, or Firm*—Graham & James LLP

[57] ABSTRACT

Cyclic AMP and cyclic GMP derivatives, such as 8-bromoadenosine-3', 5'-cyclic methylphosphonate, are effective in inhibiting phosphodiesterases.

26 Claims, No Drawings

ADENOSINE AND GUANOSINE-3'-5'-CYCLIC METHYLPHOSPHONATE DERIVATIVES

This is a continuation in part of our copending application Serial No. 996,504, filed Dec. 23, 1992, now abandoned, which is a continuation of Ser. No. 394,524, filed Aug. 16, 1989, now abandoned.

The present invention relates to cyclic adenosine-3', 5'-methylphosphonate (cAMP) derivatives and to guanosine-3', 5'-cyclic methylphosphonate (cGMP) derivatives which are useful for their pharmacological activity such as for their antidementia activity.

It is known in the art that cyclic AMP acts as a transmitter of hormones and participates in various physiological reactions in living bodies. There are, however, many questions as to its usefulness as a therapeutic agent. For example, the compound is only poorly absorbed in living bodies and, even after absorption, tends to be easily decomposed by the enzymes which are contained therein.

Dibutyryl cyclic AMP has been synthesized for the purpose of improving the cell permeability of cyclic AMP and has been used as a medicament.

A recent study described adenosine-3', 5'-cyclic methylphosphonate as possessing useful pharmacological activity (see Japanese Unexamined Patent Publication No. 135, 399/88). This study showed that cyclic AMP derivatives possessed pharmacological activities. However, the study only described one cyclic AMP derivative in which a methyl group is present as the only substituent group for the phosphoric acid moiety and nothing was disclosed with regard to other cyclic AMP derivatives.

It has now been discovered that cyclic nucleotides, particularly cyclic AMP derivatives and cyclic GMP derivatives of the formula I

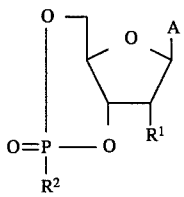

wherein $R^1$ is hydrogen, hydroxyl or acyloxy; $R^2$ is lower alkyl; and A is:

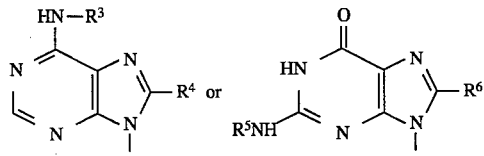

wherein $R^3$ is hydrogen, methyl or acyl; $R^4$ is hydrogen or halo; $R^5$ is hydrogen or acyl; and $R^6$ is hydrogen or halo, provided that when $R^1$ is hydroxyl and $R^2$ is methyl, A is not:

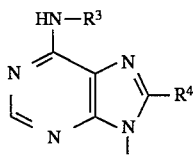

wherein $R^3$ is hydrogen and $R^4$ is hydrogen are useful as antidementia agents. Japanese Unexamined Patent Publication No. 135,399/88 describes a compound of the formula I in which $R^1$ is hydroxy, $R^2$ is methyl, A is

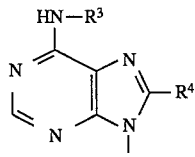

wherein $R^3$ and $R^4$ are each hydrogen.

As the result of various studies on the synthesis of various cyclic AMP and GMP derivatives and their pharmacological effects, we have now established that compounds of the formula I are useful in the treatment of dementia in humans and animals.

According to one embodiment of the present invention, $R_3$ is hydrogen, methyl or acyl of the formula —$COR^{31}$ wherein $R^{31}$ is lower alkyl or aryl. When $R^{31}$ is lower alkyl, it is preferably alkyl of 1 to 4 carbon atoms such as methyl, ethyl, propyl and butyl. When $R^{31}$ is aryl, it is preferably phenyl or naphthyl.

According to a further embodiment of the present invention, $R^4$ is hydrogen, bromo, chloro or fluoro.

According to a further embodiment of the present invention $R^5$ is hydrogen or acyl of the formula —$COR^{51}$ wherein $R^{31}$ is lower alkyl or aryl. When $R^{51}$ is lower alkyl, it is preferably alkyl of 1 to 4 carbon atoms especially methyl, ethyl, propyl and butyl. When $R^{51}$ is aryl, it is preferably phenyl or naphthyl.

According to a further embodiment of the present invention, $R^6$ is hydrogen, bromo, chloro or fluoro.

According to a further embodiment of the present invention, $R^1$ is hydrogen, hydroxyl or acyloxy.

According to a further embodiment of the present invention, $R^2$ is alkyl of 1 to 4 carbon atoms especially methyl, ethyl, propyl and butyl.

According to a further embodiment of the present invention, the compounds of formula I are in optically pure form.

Representative examples of compounds according to the present invention are those set forth below:

N-acetyladenosine-3', 5'-cyclic methylphosphonate
N-buytyryladenosine-3', 5'-cyclic methylphosphonate
N-benzoyladenosine-3', 5'-cyclic methylphosphonate
N-acetyladenosine-3', 5'-cyclic ethylphosphonate
N-butyryladenosine-3', 5'-cyclic ethylphosphonate
N-benzoyladenosine-3', 5'-cyclic ethylphosphonate
N-acetyladenosine-3' , 5'-cyclic propylphosphonate
N-butyryladenosine-3', 5'-cyclic propylphosphonate
N-benzoyladenosine-3', 5'-cyclic propylphosphonate
2-deoxyadenosine-3', 5'-cyclic methylphosphonate
N-acetyl-2'-deoxyadenosine-3', 5'-cyclic methylphosphonate
N-butyryl-2'-deoxyadenosine-3', 5' -cyclic methylphosphonate
N-benzoyl-2'-deoxyadenosine-3', 5'-cyclic methylphosphonate
N-acetyl-2'-deoxyadenosine-3', 5'-cyclic ethylphosphonate
N-bultyryl-2'-deoxyadenosine-3', 5'-cyclic ethylphosphonate
N-benzoyl-2'-deoxyadenosine-3', 5'-cyclic ethylphosphonate
N-acetyl-2'-deoxyadenosine-3', 5'-cyclic propylphosphonate
N-butyryl-2'-deoxyadenosine-3', 5'-cyclic propylphosphonate N-benzoyl-2'-deoxyadenosine-3', 5'-cyclic propylphosphonate
2'-0-butyryladenosine-3', 5'-cyclic methylphosphonate
N-acetyl-2'-0-butyryladenosine-3', 5'-cyclic methylphosphonate
N-butyryl-2'-0-butyryladenosine-3', 5'-cyclic methylphosphonate
N-benzoyl-2'-0-butyryladenosine-3', 5'-cyclic methylphosphonate
N-acetyl-2'-0-butyryladenosine-3', 5'-cyclic ethylphosphonate
N-butyryl-2'-0-butyryladenosine-3', 5'-cyclic ethylphosphonate
N-benzoyl-2'-0-butyryladenosine-3', 5'-cyclic ethylphosphonate
N-acetyl-2'-0-butyryladenosine-3', 5'-cyclic propylphosphonate
N-butyryl-2'-0-butyryladenosine-3', 5'-cyclic propylphosphonate
N-benzoyl-2'-0-butyryladenosine-3', 5'-cyclic propylphosphonate
N-acetyl-8-bromoadenosine-3', 5'-cyclic methylphosphonate
N-butyryl-8-bromoadenosine-3', 5'-cyclic methylphosphonate
N-benzoyl-8-bromoadenosine-3', 5'-cyclic methylphosphonate
N-acetyl-8-bromoadenosine-3', 5'-cyclic ethylphosphonate
N-butyryl-8-bromoadenosine-3', 5'-cyclic ethylphosphonate
N-benzoyl-8-bromoadenosine-3', 5'-cyclic ethylphosphonate
N-acetyl-8-bromoadenosine-3', 5'-cyclic propylphosphonate
N-butyryl-8-bromoadenosine-3', 5'-cyclic propylphosphonate
N-benzoyl-8-bromoadenosine-3', 5'-cyclic propylphosphonate
N-acetyl-8-bromo-2'-deoxyadenosine-3', 5'-cyclic methylphosphonate
N-butyryl-8-bromo-2'-deoxyadenosine-3', 5'-cyclic methylphosphonate
N-benzoyl-8-bromo-2'-deoxyadenosine-3', 5'-cyclic methylphosphonate
N-acetyl-8-bromo-2'-deoxyadenosine-3', 5'-cyclic ethylphosphonate
N-butyryl-8-bromo-2'-deoxyadenosine-3', 5'-cyclic ethylphosphonate
N-benzoyl-8-bromo-2'-deoxyadenosine-3', 5'-cyclic ethylphosphonate
N-acetyl-8-bromo-2'-deoxyadenosine-3', 5'-cyclic propylphosphonate
N-butyryl-8-bromo-2'-deoxyadenosine-3', 5'-cyclic propylphosphonate
N-benzoyl-8-bromo-2'-deoxyadenosine-3', 5'-cyclic propylphosphonate
N-acetyl-8-bromo-2'-butyryladenosine-3', 5'-cyclic methlyphosphonate
N-butyryl-8-bromo-2'-butyryladenosine-3', 5'-cyclic methlyphosphonate
N-benzoyl-8-bromo-2'-butyryladenosine-3', 5'-cyclic methlyphosphonate
N-acetyl-8-bromo-2'-butyryladenosine-3', 5'-cyclic ethlyphosphonate
N-butyryl-8-bromo-2'-butyryladenosine-3', 5'-cyclic ethlyphosphonate
N-benzoyl-8-bromo-2'-butyryladenosine-3', 5'-cyclic ethlyphosphonate
N-acetyl-8-bromo-2'-butyryladenosine-3', 5'-cyclic propylphosphonate
N-butyryl-8-bromo-2'-butyryladenosine-3', 5'-cyclic propylphosphonate
N-benzoyl-8-bromo-2'-butyryladenosine-3', 5'-cyclic propylphosphonate
Guanosine-3,5'-cyclic methylphosphonate
N-acetylguanosine-3', 5'-cyclic methylphosphonate
N-butyrylguanosine-3', 5'-cyclic methylphosphonate
N-benzoylguanosine-3', 5'-cyclic methylphosphonate
N-acetylguanosine-3', 5'-cyclic ethylphosphonate
N-butyrylguanosine-3', 5'-cyclic ethylphosphonate
N-benzoylguanosine-3', 5'-cyclic ethylphosphonate
N-acetylguanosine-3', 5'-cyclic propylphosphonate
N-butyrylguanosine-3', 5'-cyclic propylphosphonate
N-benzoylguanosine-3', 5'-cyclic propylphosphonate
2'-deoxyguanosine-3', 5'-cyclic methylphosphonate
N-acetyl-2'-deoxyguanosine-3', 5'-cyclic methylphosphonate
N-butyryl-2'-deoxyguanosine-3', 5'-cyclic methylphosphonate
N-benzoyl-2'-deoxyguanosine-3', 5'-cyclic methylphosphonate
N-acetyl-2'-deoxyguanosine-3', 5'-cyclic ethylphosphonate
N-butyryl-2'-deoxyguanosine-3', 5'-cyclic ethylphosphonate
N-benzoyl-2'-deoxyguanosine-3', 5'-cyclic ethylphosphonate
N-acetyl-2'-deoxyguanosine-3', 5'-cyclic propylphosphonate
N-butyryl-2,-deoxyguanosine-3', 5'-cyclic propylphosphonate
2'-0-butyrylguanosine-3', 5'-cyclic methylphosphonate
N-acetyl-2'-0-butyrylguanosine-3', 5'-cyclic methylphosphonate
N-butyryl-2'-0-butyrylguanosine-3', 5'-cyclic methylphosphonate
N-benzoyl-2'-butyrylguanosine-3', 5'-cyclic methylphosphonate
N-acetyl-2,-0-butyrylguanosine-3', 5'-cyclic ethylphosphonate
N-butyryl-2'-0-butyrylguanosine-3', 5'-cyclic ethylphosphonate
N-benzoyl 2'-0-butyrylguanosine-3', 5'-cyclic ethylphosphonate
N-acetyl-2'-0-butyrylguanosine-3', 5'-cyclic propylphosphonate
N-butyryl- 2'-0-butyrylguanosine-3', 5'-cyclic propylphosphonate
N-benzoyl-2'-0-butyrylguanosine-3', 5'-cyclic propylphosphonate
N-acetyl-8-bromoguanosine-3', 5'-cyclic methylphosphonate
N-butyryl-8-bromoguanosine-3', 5'-cyclic methylphosphonate
N-benzoyl-8-bromoguanosine-3', 5'-cyclic methylphosphonate
N-acetyl-8-bromoguanosine-3', 5'-cyclic ethylphosphonate
N-butyryl-8-bromoguanosine-3', 5'-cyclic ethylphosphonate
N-benzoyl-8-bromoguanosine-3', 5'-cyclic ethylphosphonate
N-acetyl-8-bromoguanosine-3', 5'-cyclic propylphosphonate N-butyryl-8-bromoguanosine-3', 5'-cyclic propylphosphonate N-benzoyl-8-bromoguanosine-3', 5'-cyclic propylphosphonate N-acetyl-8-bromo-2'-deoxyguanosine-3', 5'-cyclic methylphosphonate N-butyryl-8-bromo-2'-deoxyguanosine-3', 5'-cyclic methylphosphonate N-benzoyl-8-bromo-2'-deoxyguanosine-3', 5'-cyclic methylphosphonate N-acetyl-8-bromo-2'-deoxyguanosine-3', 5'-cyclic ethylphosphonate N-butyryl-8-bromo-2'-deoxyguanosine-3', 5'-cyclic ethylphosphonate N-benzoyl-8-bromo-2'-deoxyguanosine-3', 5'-cyclic ethylphosphonate N-acetyl-8-bromo-2'-deoxyguanosine-3', 5'-cyclic propylphosphonate N-butyryl-8-bromo-2'-deoxyguanosine-3', 5'-cyclic propylphosphonate N-benzoyl-8-bromo-2'-deoxyguanosine-3', 5'-cyclic propylphosphonate N-acetyl-8-bromo-2'-0-butyrylguanosine-3', 5'-cyclic methylphosphonate N-butyryl-8-bromo-2'-0-butyrylguanosine-3', 5'-cyclic methylphosphonate N-benzoyl-8-bromo-2'-0-butyrylguanosine-3', 5'-cyclic methylphosphonate N-acetyl-8-bromo-2'-0-butyrylguanosine-3', 5'-cyclic ethylphosphonate N-butyryl-8-bromo-2'-0-butyrylguanosine-3', 5'-cyclic ethylphosphonate N-benzoyl-8-bromo-2'-0-butyrylguanosine-3', 5'-cyclic ethylphosphonate N-acetyl-8-bromo-2'-0-butyrylguanosine-3', 5'-cyclic propylphosphonate N-butyryl-8-bromo-2'-0-butyrylguanosine-3', 5' -cyclic propylphosphonate N-benzoyl-8-bromo-2'-0-butyrylguanosine-3', 5'-cyclic propylphosphonate The inhibitory action of cyclic AMP-dependent phosphodiesterase was examined according to the method of W. Joseph et al ("Method in Enzmology," 38, 205), by using bovine heart cyclic AMP phosphodiesterase (manufactured by Boehringer Mannheim Co.) of Boehringer Mannheim.

To a 40 mM Tris-hydrocholoride buffer (pH=8) containing magnesium chloride at a final concentration of 5 mM and 2-mercaptoethanol at a final concentration of 3.75 mM were added 200,000 cpm of [$^3$H]-labeled cyclic AMP, 0.125 to 100 μM of cyclic AMP, 1 μg of cyclic AMP-dependent phosphodiesterase and a test compound at various concentrations (the total volume of the reaction mixture was 400 μl). After the reaction was allowed to proceed at 30° C. for 10 minutes, the reaction mixture was treated at 100° C. for 2.5 minutes so as to deactivate the enzyme. After the temperature of the reaction mixture had dropped to room temperature, 50 μg of snake venom (manufactured by Sigma Corp.) was added thereto, and the mixture was heated at 30° C. for 10 minutes to decompose 5'-AMP, which was formed by the action of cyclic AMP phosphodiesterase, to adenosine. To this was added 0.5 ml of a 1:3 Cresin:H$_2$O aqueous suspension of AG1-X2 resin (manufactured by Bio-Rad Co.) to terminate the decomposition, and the reaction mixture was allowed to stand at 4° C. for 15 minutes. Thereafter, the resulting mixture was centrifuged at 12,000 rpm for 2 minutes. The radioactivity of 55 μl of the supernatant was measured with a liquid scintillation counter, and the inhibition activity of the test compound was calculated. In the case of Compound 1, prepared in Example 1 described hereinbelow, marked inhibition activity was exhibited at a concentration of 100 μM.

Inhibitory action of the optically pure compounds of the present invention against cyclic GMP phosphodiesterase was tested by the similar manner too. It will be given as hereunder in detail.

Thus, the inhibitory action was tested in accordance with Pichard et al (J. Bio. Chem. vol. 251, page 5726, 1976) using bovine heart cyclic nucleotide phosphodiesterase (manufactured Boehringer/Mannheim). To be more precise, 50 μl of test compound to a final concentration of 10 μM and 0.1 μg of cyclic nucleotide phosphodiesterase are added to 100 μl of 40 mM Tris-hydrochloric acid buffer (pH 8.0) prepared so as to make the final concentrations of MgCl$_2$, 2-mercaptoethanol and $^3$H-cyclic GMP 5 mM, 0.25% and 1.82×10$^4$ Bq, respectively. The reaction is carried out by keeping at 30° C. for 10 minutes, the enzyme is inactivated by heating at 97° C. for 5 minutes, 50 μg of snake venom (Sigma) is added to the resulting 5'-GMP at room temperature, the mixture is kept at 30° C. for 10 minutes to decompose into guanosine, then well mixed with 50 μl of a 1:3 aqueous suspension of AG 1×8 resin (Bio-Rad) and centrifuged at 14,000 rpm for 2 minutes.

The supernatant liquid (250 μl) is subjected to the radioactivity counting by liquid scintillation counter.

The enzymatic activity decreased as a result of the addition of the present invention compound was given in percentage taking the activity where no compound was added as a standard. Said percentage is defined as an "inhibitory activity" and the result is given in Table 1.

TABLE 1

| Compound Used | Inhibitory Activity (%) |
|---|---|
| [VIII] | 46 |
| [IX] | 32 |
| [X] | 61 |
| [XI] | 31 |

Stereochemical structures of the optically pure compounds used here together with some more which were synthesized in the examples given later are as follows:

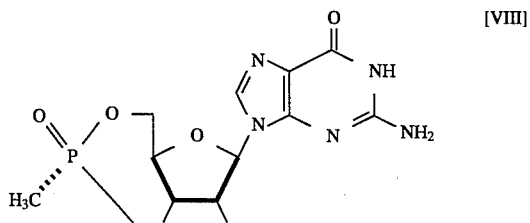

[VIII]

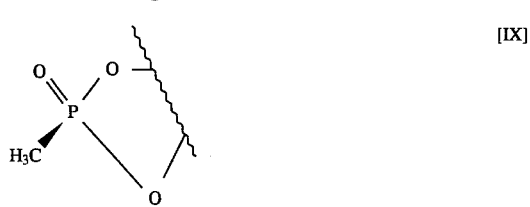

[IX]

-continued

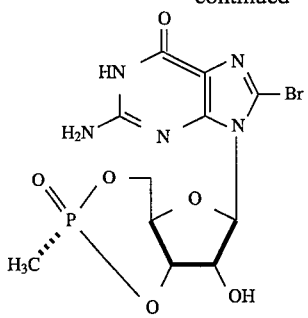

[X]

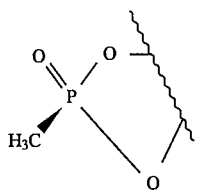

[XI]

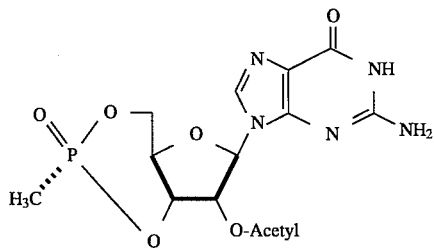

[XII]

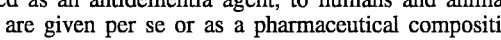

[XIII]

When the compounds of the present invention are administered as an antidementia agent, to humans and animals, they are given per se or as a pharmaceutical composition containing, for example, 0.1 to 99.5% (more preferably, 0.5 to 90%) of active ingredient in combination with a pharmaceutically acceptable carrier.

They may be given orally, parenterally, topically, or rectally. They are of course given by forms suitable for each administration route. For example, they are administered in tablets or capsule form, by injection, inhalation, eye lotion, ointment, suppository, etc. administration by injection, infusion or inhalation; topical by lotion or ointment; and rectal by suppositories. Intramuscular injection is preferred.

As to carriers, one or more liquid, solid or semisolid diluent, filler and other auxiliary agents for pharmaceutical preparations may be used. It is desired that the pharmaceutical compositions are administered in unit dosage form.

Oral administration can be effected utilizing solid and liquid dosage unit forms such as powders, tablets, capsules, granules and the like.

Powders are prepared by comminuting the compound to a suitable fine size and mixing with a similarly comminuted pharmaceutical carrier such as an edible carbohydrate as, for example, starch or mannitol. Flavoring, preservative, dispersing and coloring agents can also be present.

Capsules are made by preparing a powder mixture as described above and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder as carboxymethyl cellulose, an alginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acadia mucilage or solutions of cellulosic or polymeric materials and forcing through a screen. As an alternative to granulating, the powder mixture can be run through the tablet machine and the resulting imperfectly formed slugs broken into granules. The granules can be lubricated to prevent sticking to the tablet forming dies by means of the addition of stearic acid, a stearate salt, talc or mineral oil. The lubricated mixture is then compressed into tablets. The compounds and pharmaceuticaiiy acceptable acid addition salts of the present invention can also be combined with free flowing inert carriers and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solutions, syrups and elixirs can be prepared in dosage unit form so that a given quantity contains a predetermined amount of the compound. Syrups can be prepared by dissolving the compound in a suitably flavored aqueous solution, while elixirs are prepared through the use of a nontoxic alcoholic vehicle. Suspensions can be formulated by dispersing the compound in a nontoxic vehicle. Solubilizers and emulsifiers such as ethoxylated isostearyl alcohols and Polyoxyethylene sorbitol esters, preservatives, flavor additives such as peppermint oil or saccharin, and the like can also be added.

Where appropriate, dosage unit formulations or oral administration can be microencapsulated. The formulation can also be prepared to prolong or sustain the release as for example by coating or embedding particulate material in polymers, wax or the like.

Parenteral administration can be effected utilizing liquid dosage unit forms such as sterile solutions and suspensions intended for subcutaneous, intramuscular or intravenous injection. These are prepared by suspending or dissolving a measured amount of the compound in a nontoxic liquid vehicle suitable for injection such as aqueous or oleaginous medium and sterilizing the suspension or solution. Alternatively, a measured amount of the compound is placed in a vial and the vial and its contents are sterilized and sealed. An accompanying vial or vehicle can be provided for mixing prior to administration. Nontoxic salts and salt solutions can be added to render the injection isotonic. Stabilizers, preservatives and emulsifiers can also be added.

Rectal administration can be effected utilizing suppositories in which the compound is admixed with low-melting, water-soluble or insoluble solids such as polyethylene glycol, cocoa butter, higher esters as for example flavored aqueous solution, while elixirs are prepared through myristyl palmitate or mixtures thereof.

In determining the dosage for treating dementia a number of factors such as the age of the patient, body weight, severity of condition, administration route, and the like must be considered. Generally, from about 300 mg to 3 g per day of a compound of the present invention should be administered to a human adult preferably from 500 mg to 1 g per day. In some cases, a lower dose is sufficient and, in some other cases, a higher dose or more doses may be necessary.

It is preferred that the administration be divided so that it takes place 1 to 3 times per day.

The following nonlimitative examples more particularly illustrate the present invention.

The cyclic nucleotide derivatives according to the Present invention can be synthesized in accordance with the following reactions:

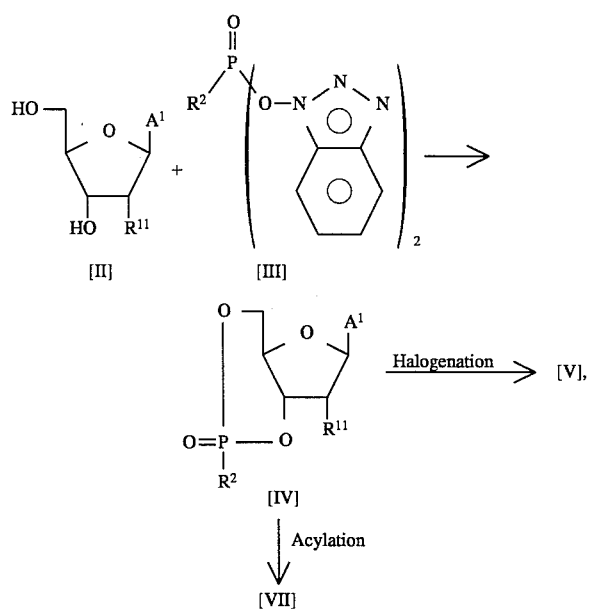

wherein $R^2$ is as above defined; $A^1$ is adenine or guanine; and $R^{11}$ is hydrogen or tetrahydropyranyloxy.

More specifically, a nucleoside of the formula [II] is reacted with an alkyl-0, 0-bis-(1-benzotriazoyl) phosphonate of the formula [III] followed by addition of a 1-alkyl imidazole, such as 1-methylimidazole, to give a cyclic derivative of the formula [IV]. If necessary the tetrahydropyranyloxy moiety in formula [IV] can be removed by reaction with an acid.

Thereafter, the acid-treated compound obtained from formula [IV] may be further subjected to halogenation or acylation to obtain a compound of the formula [V] (8-halogenoadenosine derivative), formula [VI] (a-halogeno guanosine derivative) or formula [VII] (2'-acyloxy derivative).

The starting material [II] to be used in the above process can be prepared by the method described by S. Honda et al., Tetrahedron, 40, 153–163 (1984), or by a similar method. The compound represented by General Formula [III] can be obtained from an alkylphosphonic acid dichloride and 1-hydroxybenzotriazole in accordance with the method of J. H. van Boom et al., Nucleic Acid Research, 14 2171–2185 (1986).

The reaction between Compound [II] and Compound [III] can be effected in an inactive solvent (e.g., aprotic solvent such as anhydrous dioxane, tetrahydrofuran, etc.), usually by allowing them to stand at room temperature for 30 minutes to 3 hours. Then, a 1-alkylimidazole compound is added thereto, and the resulting mixture is allowed to stand at room temperature for 5 to 24 hours.

The amount of [III] to be used is preferably from 1 to 1.2 times per mole of compound [II]. The amount of 1-alkylimidazoles to be used is 3 to 7 times per mole of the product formed by the reaction between Compounds [II] and [III].

Thereafter, a strong acid having a pH of ca. 2.0, preferably such a volatile acid as trifluoroacetic acid, hydrochloric acid, or the like, is added to the reaction mixture, and the resulting mixture is allowed to stand at a temperature of from 0° C. to room temperature for 5 to 24 hours to give the deprotected compound from [IV]. In this reaction, the acid is used usually in large excess against Compound [IV].

The deprotected compound from [IV] may be further subjected to halogenation. In the case of bromination, for example, a compound from [IV] is treated with bromine water in an acetate buffer or with bromine water alone at a temperature of 0° C. to room temperature to give Compound [V] or [VI].

The acid-treated compound from General Formula [IV] can be converted into [VII] by acylating the former with an acid halide or an acid anhydride containing an acyl group corresponding to $R^3$ or R5. This acylation can be conducted in pyridine at a temperature of from 0° C. to room temperature for a period of from a few hours to 24 hours.

The thus obtained desired compounds can be isolated and purified by known techniques, for example, by means of solvent extraction, adjustment of acidity or basicity of the solvent, solvent exchange, condensation, crystallization, recrystallization, chromatography, and the like.

The following nonlimitative examples more particularly illustrate the present invention:

The following starting materials used in the examples were prepared as follows.

N-monomethoxytrityl-2'-0-tetrahydropyranyladenosine:

This compound was prepared according to the method described by S. Honda et al., Tetrahedron, 40, 153–163 (1984).

N-benzoyl-2'-0-tetrahydropyranyladenosine:

This compound was prepared from commercially available N-benzoyadenosine according to the method of S. Honda et al. described above.

N-buty-2-0-tetrahydropyranyladenosine:

This compound was prepared in the following manner. A solution of N-benzoyl-3,5'-tetraisopropyldisoxan-1, 3-diyl-2'-0 -tetrahydropyranyl-adenosine in methanoal was treated overnight at room temperature with concentrated aqueous ammonia to give 3', 5'-tetraisopropyldisiloxan-1,3-diyl-2'-0-tetrahydopyranyladenosine, which was then treated overnight at room temperature with butyrl chrloride in pyridine to give N-butyryl-3', 5'-0 -tetraisopropyldisiloxan-1,3-diyl-2'-0-tetrahydropynanyladensoine. After the butyoyl derivative had been dissolved in 13 ml of tetrahydrofuran, 13 ml of a tetrahydrofuran solution of 1 mol of tetrabutyl ammonium fuloride was added thereto, and the mixture was stirred at room temperature for 15 minutes. After the reaction, 100 ml of a mixture of dichloromethane and pyridine (3:1) was added thereto, and the resulting mixture washed with a saturated aqueous sodium bicarbonate solution. The organic layer was dried with magnesium sulfate and concentrated to dryness. The residue was purified by silica gel chromatography (dichloromethane/methanol) to give the desired compound. N-monomethoxytrityl-2'-0-tetrahydropranylguanosine was prepared according to the method of S. Honda et al. described above.

Example 1: Sythesis of 8-bromoadenosine-3', 5'-cyclic methyl phosphonate

To 915 mg of N-monomethoxytrityl-2'-0-tetrahydropyranyladenosine was added at room temperature 20.5 ml of a 0.11M dioxane solution of methyl-0, 0-bis-(1-benzotriazolyl) phosphonate prepared by the method of J. J. van Boom et al., as described in Nucleic Acid Research, 14, 2171–2185 (1986). After 30 minutes, 1.4 ml of 1-methylimidazole was added thereto, and the reaction was allowed to proceed overnight. Thereafter, 2.0 ml of pyridine was added thereto, and the resulting mixture was distributed between dichloromethane and water (containing ⅒ volume of saturated aqueous sodium chloride solution and ⅒ volume of 1M triethyl ammonium acetate [pH=7.0]), and the organic layer was dried with magnesium sulfate and concentrated to dryness to give crude solids. The product was purified by preparative TLC to give 310 mg of white crystals.

The product (310 mg) was dissolved in 20 ml of a mixture of dioxane and water (9:1), and 0.1N hydrochloric acid was added dropwise thereto up to a pH of 2.0. This was allowed to stand overnight at room temperature. After the completion of the reaction had been confirmed by TLC, the reaction mixture was concentrated to dryness. The residue was purified by preparative TLC to give 125 mg of white solids. The product was recrystallized from a mixture of water and ethanol (5:95) to give white needles of adenosine-3', 5'-cyclic methyl phosphonate Melting point: 207°–210° C.

In 0.4 ml of 0.5M acetate buffer (pH= 4.0) was dissolved 10 mg of the compound prepared above, and 0.6 ml of bromine-water was added thereto at room temperature. After being allowed to stand for 1 hour, the reaction mixture was condensed to dryness, and the residue was purified by preparative TLC to give 11 mg of the desired compound.

TLC (methanol/dichloromethane [1:10]): Rf=0.65

$^1$H-NMR (D$_2$O) δ: 1.92 (3 H, d J=18.0 Hz P—CH$_3$), 4.35 (1 H, m, H-5a), 5.06 (1 H, d, J=6.0, H-2'), 5.47 (1 H, m, H-3'), 6.08 (1 H, s, H-1'), and 8.12 (1 H, s, Arom. H-2)

MeOH

UVλmax= 273 nm

Example 2: Synthesis of N-benzoyladenosine-3', 5'-cyclic methylphosphonate

To 93 mg of N-benzoyl-2'-0-tetrahydropyranyladenosine was added 2.7 ml of a 0.11M solution in dioxane of methyl-0, 0-bis-(1-benzotriazolly) phosphonate prepared in a similar manner as in Example 1. After the resulting mixture had been allowed to stand at room temperature for 30 minutes, 0.2 ml of 1-methylimidazole was added thereto, and the reaction was allowed to proceed overnight at room temperature. Thereafter, 1.0 ml of pyridine was added, and the resulting mixture was treated in the same manner as in Example 1 to give 40 mg of white solids of N-benzoyl-2', 0 -tetrahydropyranyladenosine-3', 5' -cyclic methlyphosphonate.

In 4.0 ml of a mixture of dioxane and water (9:1) was dissolved the above product (40 mg), and 1.4 ml of 0.1N hydrochloric acid was added dropwise at room temperature. After the reaction mixture had been allowed to stand overnight to complete the reaction, the reaction mixture was condensed to dryness, and the residue was purified by means of preparative TLC to give 32 mg of white solids.

$^1$H-NMR (CDCl$_3$/CD$_3$OD [8:2]) λ: 1.76 (3 H, d, J=18.0 P—CH$_3$), 4.30–4.70 (4 H, m), 4.84 (1 H, d, J=5.0, H-2'), 5.30 (1 H, m, H-3'), 6.11 (1 H, s, H-1 '), 7.50–7.70 (3 H, benzoyl), 8.00–8.10 (2 H, benzoyl), 8.34 (1 H, s, Arom.), and 8.76 (1 H, s, Arom.)

Example 3: Synthesis of N-butyryladenosine-3', 5'-cyclic methylphosphonate

White solids of N-butyryl-2'0-tetrahydropyranyladenosine- 3', 5'-cyclic methylphosphonate (45 mg) was prepared from 134 mg of N-butyryl-2'-0-tetrahydropyranyladenosine in a similar manner as in Example 1.

The product was subjected to acid hydrolysis in a similar manner as in Example 1 to give 30 mg of the desired compound.

$^1$ H-NMR (D$_2$O) μ: 1.00 (3 H, t, J=7.8 CH$_2$CH$_3$), 1.80 (2 H, hextet, J=7.8 CH $_2$CH$_3$), 1.86 (3 H, d, J=18.0 P—CH$_3$), 2.60 (2 H, t, J=7.8, —CO—CH$_2$—), 4.92 (1 H, d, J=4.0, H-2'), 5.20 (1 H, m, H-3'), 6.25 (1 H, s, H-1'), 8.46 (1 H, s, Arom), and 8.65 (1 H, s, Arom.)

Example 4: Synthesis of N-benzoyl-2'-0-deoxyadenosine-3', 5'-cyclic methylphosphonate To 355 mg of commercially available N-benzoyl-2'deoxyadenosine was added at room temperature 14 ml of a 0.11M solution in dioxane of methyl-0, 0-bis(1-benzotriazole) phosphonate prepared in a similar manner as in Example 1. After 30 minutes, 1.0 ml of 1-methylimidazole was added thereto. After the mixture had been further stirred overnight at room temperature, 2.0 ml of pyridine was added thereto, and the resulting mixture was distributed between 100 ml of a mixture of dichloromethane and dioxane (9:1) and a saturated aqueous sodium chloride solution. The organic layer was condensed to dryness, and the residue was purified by silica gel chromatography to give 114 mg of white solids of the desired compound.

Example 5: Synthesis of guanosine-3', 5'-cyclic methylphosphonate

To 280 mg of N-monomethoxytrityl-2'-0-tetrahydropyranylguanosine was added at room temperature 8 ml of a 0.11M solution in dioxane of methyl-0, 0-bis-(1-benzotriazole) phosphonate prepared in a similar manner as in Example 1. After 30 minutes, 0.6 ml of 1-methylimidazole was added thereto. After the reaction had been allowed to proceed overnight at room temperature, 1.0 ml of pyridine was added, and the resulting mixture was distributed between dichloromethane and a saturated sodium chloride solution. The organic layer was condensed to dryness, and the residue was purified by means of preparative TLC to give 60 mg of white solids of N-monomethoxytrityl-2'0-tetrahydropranylguanosine-3', 5'-cyclic methylphosphonate.

In 4.0 ml of a mixture of dioxane and water (9:1) was dissolved 40 mg of the compound, and the pH of the solution was adjusted to 2.0 with 0.1N hydrochloric acid. After being allowed to stand overnight at room temperature, the reaction mixture was condensed to dryness and purified by TLC to give 19 mg of the desired compound.

Melting point: 238°–240° C. (decomp.)

$^1$H-NMR (D$_2$O) δ: 1.82 (3 H, d, J=18.0 P—CH$_3$), 4.34–4.90 (4 H, m) 5.20 (1 H, m, H-3'), 5.98 (1 H, s, and H-1'), and 7.85 (1 H, s, H-8)

UVλ$_{max}$: 252 nm (ξ=13,200)

Example 6: Synthesis of 8-bromoguanosine-3', 5'-cyclic methylphosphonate

In 0.5 ml of water was added 2.0 mg of guanosine-3', 5'-cyclic methylphosphonate prepared in Example 5. To this was added 0.2 ml of bromine-water, and the reaction was allowed to proceed at room temperature for 5 minutes. It was confirmed by means of TLC that the starting material had completely disappeared [TLC: methanol/dichloromethane (2:8), Rf value of the starting material= 0.18, and Rf value of the product=0.45]. The mixture was condensed to dryness, and the residue was purified by TLC to give 2.5 mg of the desired compound. UVλpH$_{max}$1.0: 261 nm (ξ= 18,500)

Example 7: Synthesis of N-n-butyryl-2'0-n-butyryladenosine 3', 5'-cyclic methylphosphonate At room temperature, 60 μl of n-butyryl chloride was added to 0.6 ml of a pyridine solution of 5 mg of adenosine-3', 5'-cyclic methylphosphonate. After being allowed to stand overnight, the mixture was condensed to dryness, and the residue was distributed between dichloromethane and water. The organic layer was dried and condensed to dryness, and the residue was purified by preparative TLC (dichloromethane:methanol=95.5) to give 3 mg of the desired compound.

$^1$H-NMR (CDCl$_3$) δ: 1.72 (3 H, d J=19, OP—CH$_3$), 2.60 (2 H, t, NHCO—CH$_2$—), 2.84 (2 H, t, OCO—CH$_2$—), 5.28 (1 H, d, H-2' ), 6.02 (1 H, s, H-1'), 8.10 (1 H, s, Arom.), and 8.71 (1 H, s, Atom.)

Example 8: Synthesis of [VIII] and [IX]

Guanosine-3', 5'-cyclic methylphosphonate (90 mg) prepared in Example 5 was dissolved in 20 ml of water, the solution was applied to silicagel (40 ml; 20–80 μm) for reversed phase chromatography, and eluted with water, 5% aqueous methanol, 10% aqueous methanol and 15% aqueous methanol successively whereupon 8 mg of [IX] was eluted firstly and then 75 mg of [VIII] was eluted. Thus they were eluted in completely separated manner.

[VIII]: $^1$H$_{nmr}$D$_2$O (220 MHz): 1.82 (3 H, d, J=19.0, p—CH$_3$), 4.34–4.90 (55 H, m), 5.20 (1H, m, H-3'), 5.80 (1 H, s, H-1'). 7.86 (1 H, s, H-8).

[IX]: $^1$H D$_2$O (220 MH$_3$): 188 (3 H, d, J= 18.0, p—CH$_3$), 4.34–4.90 (5 H, m), 6.02 (1 H, s, H-1), 7.86 (1 H, s, H-8').

Example 9: Synthesis of [X] and [XI]

[VIII] (32 mg) prepared in Example 8 was made to react with 1.0 ml bromine water at room temperature for 5 minutes in 1.0 ml of water. Bromine was evaporated using an aspirator, the resulting precipitate was collected, washed with cold water and rinsed with acetone to give 30 mg of [X], yellow powder.

Similarly prepared was 28 mg [XI], yellow powder, from 32 mg of [IX].

Example 10: Synthesis of [XII]

[VIII] (30 mg) prepared in Example 8 was allowed to stand overnight with a mixture of 0.5 ml of acetic anhydride and 1.0 ml of pyridine at room temperature, the reaction mixture was concentrated in vacuo followed by evaporating to dryness and the residue was pulverized with a 100:5:0.5 mixture of n-hexane, dichloromethane and methanol to give 32 mg of [XII].

$^1$H$_{nmr}$CD$_3$OD—CDCl$_3$ (1:1) (220 MHz): 1.75 (3 H, d, J=18.0, p—CH$_3$), 2.20 (3 H, s, OCOCH$_3$), 4.00–4.65 (3 H, m), 5.80 (1 H, d, J=8.0, H-1'), 5.75–5.85 (2 H, m, H-2', 3'overlapped with H-1'), 7.60 (1 H, bs, H-8).

Example 11: Synthesis of [XIII]

[VIII] (30 mg) prepared in Example 8 was suspended in 3.0 ml of pyridine and made to react with 72 mg of palmitoyl chloride for 12 hours. After the reaction, the mixture was concentrated and partitioned between dichloromethane and diluted hydrochloric acid. The organic layer was concentrated and evaporated to dryness. The residue was purified with preparative TLC (20×20 cm; 2 mm thickness) using 5% methanolomethylene dichloride as a developing solvent to give 40 mg of [XIII].

Example 12: Comparison and measurement of PDE I activities

In order to specifically demonstrate the efficacy of the claimed compounds over the compound of Japanese Application JA 63- 135399 (adenosine-3', 5'-cyclic methylphosponate), the inhibitory effects of 8-bromoadenosine-3', 5'-cyclic methylphosphonate, of Example 1, have been compared against the compound of JA 63-135399, on bovine heart phosphodiesterase I (PDE I). PDE I activities were measured by the slightly modified method of Thompson et al., *Biochemistry*, 18: 5228 (1979), as follows.

In the first step, the reaction mixture was composed of the following in a final volume of 0.4 ml: 35 MM Tris-HCl buffer (pH 8.0), 10 mM MgCl$_2$, 5 mM 2-mercaptoethanol, 75 ng bovine serum albumin, 30 ng calmodulin, 2.25 mM CaCl$_2$ and 0.1 μCi [ $^3$H] cAMP. The test compounds were dissolved in dimethyl sulfoxide (DMSO) to make the concentration of 200 mM. The stock solution was diluted with DMSO to prepare direct concentrations. The final concentration of DMSO in the assay mixture was adjusted to 0.5%. The reaction was initiated by the addition of 40 μg PDE I (Boehringer-Mannheim-Yamanouchi Co., Ltd., Tokyo, Japan). After incubation at 30° C. for 10 min., the reaction was stopped by boiling 5 min. and then the mixtures were cooled in an ice bath.

In the second step, 0.1 ml of 1 mg/ml snake venom nucleotidase (Sigma Chemical Company, USA) was added into the cooled mixture obtained above. The mixture was incubated at 30° for 10 min. This incubation was terminated by the addition of 1.0 ml of slurry resin (1:3) (AGI-x2, Bio-Rad). After allowing this to stand at room temperature for about 1 hr., the mixtures were centrifuged at 4,000 rpm for 15 min. An aliquot (0.4 ml ) of the supernatant was transferred into a vial to count the radioactivities. The activities were measured by a liquid scintillation counter (Aloka). The inhibitory effects of the test compounds on bovine heart PDE I were represented as IC$_{50}$ values and are shown below in Table 2.

TABLE 2

Inhibition of PDE I

| Compounds | Inhibition IC$_{50}$, μM) |
|---|---|
| Adenosine-3',5'-cyclic methylphosphonate (The compound of JA 63-135399) | 2880 |
| 8-bromoadenosine-3,5'-cyclic methylphosphonate (The compund of Example I) | 442 |

The inhibitory activity of the claimed compound (8 -bromoadenosine-3', 5'-cyclicmethylphosphonate) is nearly seven times greater than that of the compound of JA 63-135399.

What is claimed is:

1. A compound of the formula

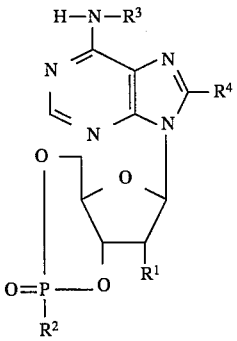

wherein $R^1$ is hydrogen, hydroxyl or acyloxy; $R^2$ is lower alkyl; $R^3$ is hydrogen, methyl or acyl; and $R^4$ is hydrogen or halo; provided that when $R^1$ is hydrogen and $R^2$ is lower alkyl, $R^3$ and $R^4$ are not both hydrogen.

2. A compound according to claim 1 wherein $R^3$ is hydrogen, methyl or acyl of the formula —COR$^{31}$ wherein $R^{31}$ is lower alkyl or aryl.

3. A compound according to claim 2 wherein $R^{31}$ is alkyl of 1 to 4 carbon atoms.

4. A compound according to claim 2 wherein $R^{31}$ is phenyl or naphthyl.

5. A compound according to claim 1 wherein $R^4$ is hydrogen, bromo, chloro or fluoro.

6. A compound according to claim 1 wherein $R^6$ is hydrogen, bromo, chloro or fluoro.

7. A compound according to claim 1 wherein $R^2$ is alkyl of 1 to 4 carbon atoms.

8. A pharmaceutical composition which comprises a compound of the formula

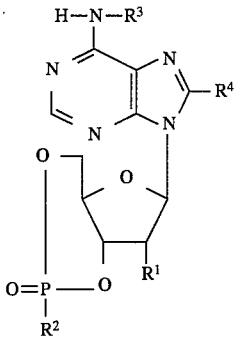

wherein $R^1$ is hydrogen, hydroxyl or acyloxy; $R^2$ is lower alkyl; $R^3$ is hydrogen, methyl or acyl; and $R^4$ is hydrogen or halo; provided that when $R^1$ is hydrogen and $R^2$ is lower alkyl, $R^3$ and $R^4$ are not both hydrogen in combination with a pharmaceutically acceptable carrier.

9. A composition according to claim 8 wherein $R^{31}$ is hydrogen, methyl or acyl of the formula —COR$^{31}$ wherein $R^{31}$ is lower alkyl or aryl.

10. A composition according to claim 9 wherein $R^{31}$ is alkyl of 1 to 4 carbon atoms.

11. A composition according to claim 9 wherein $R^{31}$ is phenyl or naphthyl.

12. A composition according to claim 8 wherein $R^4$ is hydrogen, bromo, chloro or fluoro.

13. A pharmaceutical composition which comprises a compound of the formula

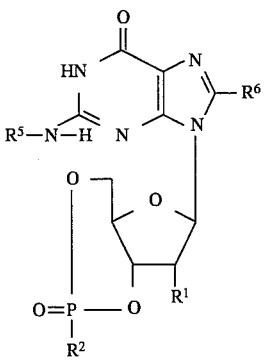

wherein $R^1$ is hydrogen, hydroxyl or acyloxy; $R^2$ is lower alkyl; R5 is hydrogen or acyl and $R^6$ is hydrogen or halo in combination with a pharmaceutically acceptable carrier.

14. A composition according to claim 13 wherein $R^5$ is hydrogen or acyl of the formula —COR$^{51}$ wherein $R^{51}$ is lower alkyl or aryl.

15. A composition according to claim 14 wherein $R^{51}$ is alkyl of 1 to 4 carbon atoms.

16. A composition according to claim 14 wherein $R^{51}$ is phenyl or naphthyl.

17. A composition according to claim 13 wherein $R^6$ is hydrogen, bromo, chloro or fluoro.

18. A composition according to claim 8 wherein $R^2$ is alkyl of 1 to 4 carbon atoms.

19. A compound of the formula

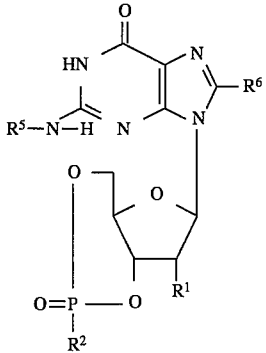

wherein $R^1$ is hydrogen, hydroxyl or acyloxy; $R^2$ is lower alkyl; $R^5$ is hydrogen or acyl and $R^6$ is hydrogen or halo.

20. A compound according to claim 19 wherein $R^1$ is hydroxyl or acyloxy.

21. A compound according to claim 19 wherein $R^2$ is alkyl of 1 to 4 carbon atoms.

22. A composition according to claim 13 wherein $R^1$ is hydroxyl or acyloxy.

23. A composition according to claim 13 wherein $R^2$ is alkyl of 1 to 4 carbon atoms.

24. A compound according to claim 19 wherein $R^5$ is hydrogen or acyl of the formula —$COR^{51}$ wherein $R^{51}$ is lower alkyl or aryl.

25. A compound according to claim 24 wherein $R^{51}$ is alkyl of 1 to 4 carbon atoms.

26. A compound according to claim 24 wherein $R^{51}$ is phenyl or naphthyl.

* * * * *